United States Patent [19]

Mori et al.

[11] Patent Number: 5,672,766
[45] Date of Patent: Sep. 30, 1997

[54] METHOD FOR PRODUCING ALDEHYDES

[75] Inventors: Tomoyuki Mori; Masaki Takai; Tomohiko Inoue, all of Okayama, Japan

[73] Assignee: Mitsubishi Chemical Corporation, Tokyo, Japan

[21] Appl. No.: 568,970

[22] Filed: Dec. 7, 1995

[30] Foreign Application Priority Data

Dec. 12, 1994 [JP] Japan ............... 6-307707
Apr. 4, 1995 [JP] Japan ............... 7-079052

[51] Int. Cl.$^6$ ............... C07C 45/50
[52] U.S. Cl. ............... 568/454; 568/455
[58] Field of Search ............... 568/454

[56] References Cited

U.S. PATENT DOCUMENTS

| 4,258,215 | 3/1981 | Dawes et al. | 568/454 |
|---|---|---|---|
| 4,482,749 | 11/1984 | Dennis et al. | |
| 4,496,768 | 1/1985 | Dennis et al. | |
| 4,567,306 | 1/1986 | Dennis et al. | 568/455 |
| 4,599,206 | 7/1986 | Billig et al. | |
| 4,668,651 | 5/1987 | Billig et al. | |
| 4,769,498 | 9/1988 | Billig et al. | 568/454 |
| 4,885,401 | 12/1989 | Billig et al. | |
| 5,235,113 | 8/1993 | Sato et al. | |
| 5,288,918 | 2/1994 | Maher et al. | |
| 5,391,801 | 2/1995 | Sato et al. | |
| 5,426,238 | 6/1995 | Mori et al. | |

FOREIGN PATENT DOCUMENTS

| 62-116587 | 11/1987 | Japan. |
|---|---|---|
| 4-290551 | 8/1992 | Japan. |
| 5-48215 | 3/1993 | Japan. |
| 5-187779 | 7/1993 | Japan. |
| WO87/07261 | 12/1987 | WIPO. |

*Primary Examiner*—C. Warren Ivy
*Assistant Examiner*—Sreeni Padmanabhan
*Attorney, Agent, or Firm*—Oblon, Spivak, McClelland, Maier & Neustadt, P.C.

[57] ABSTRACT

A method for producing aldehydes, which comprises reacting an olefinic unsaturated compound with carbon monoxide and hydrogen for hydroformylation in the presence of a rhodium-phosphite complex catalyst to obtain a reaction product solution containing the rhodium-phosphite complex catalyst and an aldehyde product, and separating from the reaction product solution at least one component selected from the group consisting of carbon monoxide, hydrogen, an unreacted olefinic unsaturated compound, the aldehyde product, a solvent, a medium-boiling by-product and a high-boiling by-product by a separating operation, wherein at least one separating operation is carried out substantially in the absence of water, and the temperature and the residence time in the separating operation are selected to be within such ranges that value P calculated from the following formula (1) would be at most 1:

$$P = 5.0 \times 10^5 \times \exp[-5000/(T_1 + 273)] \times \theta T_1 \qquad (1)$$

where $T_1$ is the maximum temperature (°C.) in the separating operation, and $\theta T_1$ is the residence time (minutes) of the liquid in the separating operation.

28 Claims, No Drawings

METHOD FOR PRODUCING ALDEHYDES

BACKGROUND OF THE INVENTION

1. Field of the Invention

The present invention relates to a method for producing aldehydes by subjecting an olefinic unsaturated compound to a hydroformylation reaction in the presence of a rhodium-phosphite complex catalyst.

2. Discussion of Background

A process for producing aldehydes which comprises reacting an olefinic unsaturated compound with carbon monoxide and hydrogen in the presence of a Group 8 metal complex catalyst, is widely practiced on an industrial scale. As a catalyst for this hydroformylation reaction, it is common to employ a complex catalyst having a Group 8 metal such as rhodium modified with a ligand such as a trivalent phosphorus compound. In order to improve the activity or selectivity for the hydroformylation reaction, various ligands have been studied. For example, Japanese Examined Patent Publication No. 10730/1970 discloses that a rhodium catalyst modified with a trivalent phosphorus ligand such as as a triaryl phosphine or a triaryl phosphite, is effective.

Among various catalysts, a catalyst modified with a phosphite ligand is known to show a high catalytic activity and excellent selectivity in the hydroformylation reaction.

However, as disclosed in Japanese Unexamined Patent Publication No. 51229/1984, with a phosphite ligand such as triphenyl phosphite, it is known that the ligand is relatively quickly decomposed in the hydroformylation reaction system, whereby the catalytic activity will decrease, and it is therefore necessary to continuously supplement the phosphite ligand. Accordingly, for the purpose of not only improving the activity and selectivity of the catalyst but also minimizing the decrease of the catalytic activity due to the loss of the phosphite ligand, various phosphite ligands have been proposed.

For example, Japanese Unexamined Patent Publications No. 51228/1984 and No. 51230/1984 disclose methods of employing cyclic phosphite ligands containing a phosphorus atom at a bridge head portion. Further, Japanese Unexamined Patent Publication No. 123134/1982 discloses a method of employing a triaryl phosphite ligand having a substituent at a specific position of the benzene ring, and Japanese Unexamined Patent Publication No. 288033/1992 by the present applicant discloses a method of employing a triaryl phosphite ligand having a substituent at a specific position of the naphthyl ring. Still further, Japanese PCT Publication No. 501268/1986 discloses a method of employing a diorgano phosphite ligand having a cyclic structure containing a phosphorus atom in its molecule.

Further, with respect to bisphosphite ligands and polyphosphite ligands, Japanese Unexamined Patent Publications No. 116535/1987 and No. 116587/1987 disclose methods of employing diorgano phosphite ligands, Japanese Unexamined Patent Publication No. 290551/1992 discloses a method of employing a bisphosphite ligand having a cyclic structure, and Japanese Unexamined Patent Publication No. 178779/1993 by the present applicant discloses a method of employing a bisphosphite ligand and a polyphosphite ligand having no cyclic structure.

Such phosphite ligands show high catalytic activities and excellent selectivity in the hydroformylation reaction. Nevertheless, they have a problem in the stability of the above phosphite ligands themselves, in order to produce aldehydes industrially advantageously. Such rapid decomposition of phosphite ligands not only adversely affects the activities or stability of the catalyst but also brings about a drawback that it is necessary to continuously supplement fresh phosphite ligands.

In addition to the above-mentioned Japanese Unexamined Patent Publication No. 51229/1984, for example, Japanese PCT Publication No. 501268/1986 discloses that triphenyl phosphite readily reacts with aldehyde at room temperature even in the absence of rhodium. This drawback resulting from the use of a triorgano phosphite is believed to be attributable to the very high affinity of the phosphite to react with aldehyde, and it is known that the product obtained by the reaction will readily be hydrolyzed to form the corresponding hydroxyalkyl phosphonic acid.

Such a hydroxyalkyl phosphonic acid is formed by a self-catalyzing process and is likely to be readily formed in a continuous catalyst-recycling process wherein the phosphite ligand and the aldehyde product will be in contact with each other for a long period of time. This hydroxyalkyl phosphonic acid not only accelerates the decomposition of the ligand but also brings about a drawback such that since it is insoluble in a usual liquid hydroformylation reaction medium, it is rapidly accumulated to precipitate a gelatin-like by-product, which in turn is likely to clog or contaminate the recycling pipeline for a continuous hydroformylation reaction system. In order to remove such precipitates by an optional method such as a method of extraction of an acid by a weak base such as sodium bicarbonate, it has been necessary to stop the operation of the process periodically.

These phenomena may be regarded as characteristics specific to phosphite type ligands, which are not observed with a phosphine type ligand such as triphenyl phosphine which has heretofore been industrially used.

On the other hand, in a case where the rhodium complex catalyst is used on an industrial scale, it is essential to reuse the catalyst by continuously recycling it, since rhodium is expensive. To recycle the catalyst, it is essential to separate the catalyst solution from the reaction product. As a method for separating the catalyst, it is common to employ distillation. For example, Japanese Unexamined Patent Publication No. 159841/1980 discloses that a rhodium-phosphine catalyst shows no deterioration in the catalytic activity within the distillation temperature range of from about 20° to 350° C. Whereas, a rhodium-phosphite complex is known to decompose even under a hydroformylation reaction condition of 160° C.

Further, it is known that the phosphite type ligand is more readily decomposed in a separation step after the hydroformylation reaction step, where no oxo gas is present.

Thus, in a case where a rhodium-phosphite ligand type complex catalyst is used in a continuous recycling process, the low stability of the phosphite ligand in the separation of the catalyst is a serious problem. As a method for solving such a stability problem, e.g. Japanese Unexamined Patent Publication No. 156636/1985 discloses a method of adding a tertiary amine to neutralize an acidic substance formed by the decomposition of the phosphite ligand and a method for stabilizing the ligand by providing a tertiary amine in the hydroformylation reaction zone containing a cyclic phosphite ligand. Japanese Unexamined Patent Publication No. 156636/1985 discloses that if a tertiary amine is added to a hydroformylation reaction medium containing a non-cyclic phosphite ligand such as triphenyl phosphite, decomposition of the ligand can not be stopped, and the catalyst loses stability in a few hours and further that as a result of an experiment, it has been found that the effect of the tertiary amine for stabilizing the ligand appears only in a case of a cyclic phosphite ligand, and no effect is observed in a case of a non-cyclic phosphite ligand. Further, the above-mentioned Japanese PCT Publication No. 501268/1986 discloses a method of suppressing the decomposition to the minimum level by treatment with a weakly basic anion exchange resin. Still further, U.S. Pat. No. 4,774,361 discloses that metallization of rhodium can be suppressed by conducting the distillation in the presence of an organic polymer having certain specific polar functional groups and that separation by distillation of an aldehyde product from a product solution containing a rhodium-phosphite complex catalyst is preferably carried out at a temperature lower than 150° C., more preferably lower than 140° C.

As described above, conventional techniques require certain additives or post treatment, and a method of suppressing decomposition of a phosphite ligand has not yet been found for a recycling process employing a phosphite complex catalyst, particularly in the separation step after the reaction.

Further, as a result of the study by the present inventors, it has been found that the phosphite ligand produces a larger amount of by-products such as high boiling substances than the phosphine ligand. Such by-products tend to be formed not only in the hydroformylation reaction but also in each separation step. Formation of such by-products not only brings about a decrease in the yield of aldehyde as the desired product but also causes a decrease in the activity for reaction or a decrease in the stability of the phosphite ligand. Accordingly, in order to use the phosphite ligand on an industrial scale, a due attention has to be paid to the stability of the phosphite ligand and formation of by-products such as high boiling substances.

Further, a method for effectively suppressing decomposition of the phosphite ligand has not yet been found in the separation step in a recycling process employing a rhodium-phosphite complex catalyst having a phosphite compound containing no ring structure containing a phosphorus atom in its molecule (hereinafter referred to as a non-cyclic phosphite).

SUMMARY OF THE INVENTION

It is an object of the present invention to provide effective separating conditions for separating the aldehyde product and high boiling substances from a reaction product solution obtained by a hydroformylation reaction, while suppressing decomposition of the phosphite ligand, in a liquid recycling process using a rhodium-phosphite complex as a catalyst.

The present inventors have conducted extensive studies with the above object and as a result, have found that at the time of separating an aldehyde product or high boiling substances from a reaction product solution obtained by a hydroformylation reaction, the temperature and the residence time in the separating operation, as well as the steam fraction, in the case where the separating operation is carried out substantially in the presence of water, are responsible factors for giving an influence over the stability of the phosphite ligand and over formation of by-products such as high boiling substances. On the basis of this discovery, they have established a method whereby a loss of the phosphite ligand and formation of by-products can effectively be suppressed by conducting the separating operation under a condition such that at least the above temperature and the residence time as well as the steam fraction would be within certain specific ranges, without requiring any special additives or post treatment, and thus the present invention has been accomplished.

Namely, in one aspect, the present invention provides a method for producing aldehydes, which comprises reacting an olefinic unsaturated compound with carbon monoxide and hydrogen for hydroformylation in the presence of a rhodium-phosphite complex catalyst to obtain a reaction product solution containing the rhodium-phosphite complex catalyst and an aldehyde product, and separating from the reaction product solution at least one component selected from the group consisting of carbon monoxide, hydrogen, an unreacted olefinic unsaturated compound, the aldehyde product, a solvent, a medium-boiling by-product and a high-boiling by-product by a separating operation, wherein at least one separating operation is carried out substantially in the absence of water, and the temperature and the residence time in the separating operation are selected to be within such ranges that value P calculated from the following formula (1) would be at most 1:

$$P=5.0\times 10^3 \times \exp[-5000/(T_1+273)]\times \theta T_1 \qquad (1)$$

where $T_1$ is the maximum temperature (°C.) in the separating operation, and $\theta T_1$ is the residence time (minutes) of the liquid in the separating operation.

Further, in a second aspect, the present invention provides a method for producing aldehydes, which comprises reacting an olefinic unsaturated compound with carbon monoxide and hydrogen for hydroformylation in the presence of a rhodium-phosphite complex catalyst to obtain a reaction product solution containing the rhodium-phosphite complex catalyst and an aldehyde product, and separating from the reaction product solution at least one component selected from the group consisting of carbon monoxide, hydrogen, an unreacted olefinic unsaturated compound, the aldehyde product, a solvent, a medium-boiling by-product and a high-boiling by-product by a separating operation, wherein at least one separating operation is carried out substantially in the presence of water, and the temperature, the residence time and the steam fraction are selected to be within such ranges that value P calculated from the following formula (3) would be at most 1:

$$P=1.0\times 10^6 \times \exp[-6000/(T_2+273)]\times \theta T_2 \times X \qquad (3)$$

where $T_2$ is the maximum temperature (°C.) in the separating operation, $\theta T_2$ is the residence time (minutes) of the liquid in the separating operation, and X is the steam fraction defined by (the amount of steam)/(the amount of feed+the amount of steam).

DETAILED DESCRIPTION OF THE PREFERRED EMBODIMENTS

Now, the present invention will be described in detail. The present invention is applicable to the above-mentioned liquid catalyst recycling process wherein a catalyst is continuously used by recycling. The separating operation for separating the aldehyde product or the high boiling substance from the reaction product solution obtained by the hydroformylation reaction is meant for every separating operation employed in a common liquid catalyst recycling process. Specifically, it includes distillation operations such as simple distillation, reduced pressure distillation, thin film distillation and steam distillation as well as other separating operations such as gas-liquid separation, evaporation, gas stripping, gas absorption and extraction. The respective separating operations may be conducted by respectively independent steps, or separation of two or more components can be carried out simultaneously.

Among these separating operations, typical ones are distillation and evaporation. Firstly, separation by distillation in a liquid catalyst recycling process will be described. As a solvent for the reaction, it is usual to employ a solvent having a higher boiling point than the aldehyde product, and a catalyst and a ligand are dissolved in this solvent to obtain a solution which is used as a catalyst solution. This catalyst solution, an olefinic unsaturated compound (hereinafter sometimes represented by an olefin) and oxo gas are supplied to a usual continuous reactor and subjected to a hydroformylation reaction at a predetermined temperature under a predetermined pressure. The reaction product solution withdrawn from the reactor is separated by distillation into an unreacted olefin, and the aldehyde product and the catalyst solution. The catalyst solution containing the phosphite complex is recycled to the reactor. Further, a part of the catalyst solution is continuously or intermittently purged from the reaction system as a waste catalyst solution in order to prevent accumulation of a deactivated catalyst and a high boiling by-product, and the corresponding amounts of fresh catalyst and ligand are supplied to the reaction system.

Now, a case of evaporation will be described. Recovery of the formed aldehyde is carried out by evaporation. As a solvent for reaction, it is usual to employ a high boiling organic compound consisting of a polymer or condensed product of the aldehyde product, and a catalyst and a ligand are dissolved in this solvent to obtain a solution which is used as a catalyst solution. Into a reactor containing this catalyst solution, an olefin and oxo gas are supplied to conduct a hydroformylation reaction at a predetermined temperature under a predetermined pressure. The formed aldehyde is withdrawn from the reactor, for example, by stripping with an unreacted gas containing an unreacted olefin, carbon monoxide and hydrogen. At the same time, a part of the formed high boiling by-product will be withdrawn from the reactor together with the unreacted gas. It is preferred that the entire amount of the high boiling by-product is withdrawn from the reactor. In such a case, the amount of the high boiling by-product purged from the reaction system together with the waste catalyst is substantially the same as the formed amount. If the high-boiling by-product is withdrawn together with the unreacted gas from the reactor in an amount far larger than the formed amount, a part of the withdrawn high-boiling by-product will be recycled to the reactor in order to maintain the amount of the catalyst solution to a constant level.

By this evaporation method, the amount of the catalyst solution in the hydroformylation reactor is maintained at a constant level. A liquid substance (mainly aldehyde) in the gas mixture withdrawn from the reactor is separated from the unreacted gas by cooling or condensation. A part of the unreacted gas is purged primarily to prevent accumulation of a hydrogenation by-product such as paraffin, and the rest is recycled to the reactor. Further, a part of the catalyst solution in the reactor is continuously or intermittently purged as a waste catalyst in order to prevent accumulation of a deactivated catalyst and a high boiling by-product, and fresh catalyst and ligand are supplied to the reaction system in an amount necessary to supplement the loss by such purging.

The present invention is characterized in that among operation conditions for the above described separating operation, the temperature and the residence time are particularly selected to be within certain ranges defined by a specific formula, whereby the loss of the phosphite ligand, formation of by-products and decrease of the reaction activity can be suppressed to the minimum levels without requiring any specific additive or post treatment.

When distillation is employed as the separating operation, a temperature within a range of from 50° to 130° C. is preferred as a distillation condition as described above and as disclosed in U.S. Pat. No. 4,774,361. However, from the study by the present inventors, it has been found that even within the above temperature range, if it takes a long time for the distillation step, formation of by-products and substantial decomposition of the phosphite ligand are observed. On the contrary, it has been found that even at a temperature exceeding 150° C., if the distillation is carried out in a very short period of time, no loss of the phosphite ligand is observed. This indicates that the separating conditions not to cause a phosphite loss are determined not only by the temperature, but at least the temperature and the residence time are involved. The present inventors have found that the factors relating to formation of by-products are the temperature, the residence time, the catalyst concentration and the aldehyde concentration. From the study by the present inventors, it has been found that the relation of these factors can be represented by the following formula:

Formed amount of by-products =

$A \times$ (aldehyde concentration)$^a$(catalyst concentration)$^b \times$ (residence time) $\times \exp(-B/\text{absolute temperature})$ where A and B are constants. Here, from the study by the present inventors, it has been found that in a rhodium-phosphite catalyst system, $A=1\times10^8$ to $2\times10^8$, $a=0.5$, and $b=1.7$.

In general, an operation at a low temperature for a short residence time at a low catalyst concentration and a low aldehyde concentration suppresses formation of by-products from the phosphite ligand and the aldehyde and decomposition of the phosphite. From the study by the present inventors, it has been found that in a rhodium-phosphite catalyst system, the temperature T and the residence time $\theta T$ give a far larger influence than other factors. Accordingly, the two factors of the above-mentioned temperature T and residence time $\theta T$ are in combination related to the stability of the phosphite ligand, and the stability of the phosphite can be anticipated from the interrelation of these two factors. Namely, in a separating operation conducted substantially in the absence of water, the interrelation for suppressing the loss of the phosphite, formation of by-products and decrease of the activity to the minimum levels is within such a range that value P calculated from the following formula (1) would be at most 1:

$$P=5.0\times10^3\times\exp[-5000/(T_1+273)]\times\theta T_1 \qquad (1)$$

where $T_1$ is the maximum temperature (°C.) in the separating operation, and $\theta T_1$ is the residence time (minutes) of the liquid in the separating operation.

Further, the temperature and the residence time in the separating operation are preferably selected within such ranges that value P calculated from the following formula (2) would be at most 1:

$$P=9.6\times10^3\times\exp[-5000/(T_1+273)]\times\theta T_1 \qquad (2)$$

where $T_1$ is the maximum temperature (°C.) in the separating operation, and $\theta T_1$ is the residence time (minutes) of the liquid in the separating operation.

The temperature $T_1$ in the separating operation is preferably selected within a range of from 30° to 160° C., more preferably at most 110° C., most preferably at most 90° C. The residence time $\theta T_1$ is preferably selected within a range of from 0.01 second to 180 minutes, and the value P is preferably selected within a range of from $1.0\times10^{-7}$ to 1.

In a case where an operation of separating an unreacted olefinic unsaturated compound or the aldehyde product by distillation, such as a method of withdrawing the olefin or the aldehyde product from the reactor by gas stripping, is employed as the separating operation, or in a case where a cyclic or non-cyclic bisphosphite compound is used as the phosphite ligand for a rhodium complex catalyst, it is preferred to control the conditions within the ranges defined by the above formula (1) or (2).

According to the present invention, even in a separating operation where a high boiling catalyst solution is to be separated, for example, in a case where a film evaporator is used, the catalyst can be recycled constantly if the conditions are controlled within the ranges defined by the above formula.

On the other hand, in a case of recovering a relatively high boiling aldehyde in the presence of the phosphite ligand, steam distillation is usually employed. However, as compared with a case of usual distillation, a far greater loss of the phosphite is observed. This is believed to be attributable to the fact that the above-mentioned side reaction for forming a hydroxyalkyl sulfonic acid is accelerated by steam. Also against this phenomenon, the decomposition of the phosphite can be suppressed to a minimum level by selecting the steam distillation condition within a certain range defined by a specific formula.

The present inventors have found that in a separating operation conducted substantially in the presence of water such as steam distillation, hydrolysis of the phosphite takes place, and in addition to the temperature T and the residence time $\theta T$, the steam fraction X gives a substantial influence over the stability of the phosphite, and the stability of the phosphite ligand can be anticipated by a specific formula wherein these three factors are interrelated.

Namely, the interrelation for suppressing the loss of the phosphite, formation of by-products and decrease of the activity to the minimum levels in a separating operation conducted substantially in the presence of water, such as steam distillation, is within such a range that value P calculated from the following formula (3) would be at most 1:

$$P=1.0\times10^6\times\exp[-6000/(T_2+273)]\times\theta T_2\times X \quad (3)$$

where $T_2$ is the maximum temperature (°C.) in the separating operation, $\theta T_2$ is the residence time (minutes) of the liquid in the separating operation, and X is the steam fraction defined by (the amount of steam)/(the amount of feed+the amount of steam).

Further, the maximum temperature, the residence time and the steam fraction in the above separating operation are preferably selected within such ranges that value P calculated from the following formula (4) would be at most 1:

$$P=1.8\times10^6\times\exp[-6000/(T_2+273)]\times\theta T_2\times X \quad (4)$$

where $T_2$ is the maximum temperature (°C.) in the separating operation, $\theta T_2$ is the residence time (minutes) of the liquid in the separating operation, and X is the steam fraction defined by (the amount of steam)/(the amount of feed+the amount of steam).

Further, it is preferred that the above separating operation is steam distillation. $T_2$ is the bottom temperature (°C.) for the steam distillation, and the residence time $\theta T_2$ is the residence time (minutes) of the liquid in the distillation still.

Further, in the separating operation, the temperature $T_2$ (°C.) is selected preferably within a range of from 40° to 180° C., more preferably at most 110° C., most preferably at most 90° C. The residence time $\theta T_2$ is selected preferably from 0.01 second to 180 minutes. Likewise, the steam fraction X is selected preferably within a range of from 0.1 to 0.9. The value P is selected preferably within a range of from $1.0\times10^{-7}$ to 1.

Further, in a case where an operation for separating the aldehyde product is employed as the separating operation, or in a case where a cyclic or non-cyclic monophosphite compound is used as the phosphite ligand for the rhodium complex catalyst, it is preferred to control the conditions within the ranges defined by the above formula (3) or (4).

As the rhodium-phosphite complex catalyst to be used in the present invention, those disclosed in the above-mentioned references may be employed, and as disclosed in these references, the complex may be formed in the hydroformylation reaction system.

As a phosphite ligand forming a complex with the rhodium catalyst or as a free phosphite ligand, any optional phosphite compound such as a triaryl phosphite, a trialkyl phosphite or an arylalkyl phosphite, may be used. Further, a bisphosphite or polyphosphite compound having a combination of such phosphites in the same molecule, may also be employed.

As mentioned above, a compound such as triphenyl phosphite readily reacts with an aldehyde compound even at room temperature, thus leading to a loss of the ligand. Accordingly, among phosphite compounds, preferred for the purpose of the present invention is a phosphite compound whereby the reaction with aldehyde or water is suppressed by e.g. a steric hindrance in the molecular structure to improve the stability. For example, it is preferred to employ a phosphite compound where at least one alcohol component of the phosphite compound is an aromatic alcohol having a hydroxyl group directly bonded to the aromatic ring and having a hydrocarbon substituent on a carbon atom adjacent to the carbon atom bonded to the hydroxyl group.

For example, such phosphite compounds may be classified into the following two compound groups. One compound group is phosphite compounds having no cyclic structure containing a phosphorus atom in their molecules (hereinafter referred to as non-cyclic phosphites). The other compound group is phosphite compounds having a cyclic structure containing a phosphorus atom in their molecules (hereinafter referred to as cyclic phosphites).

Firstly, as an example for such a non-cyclic phosphite compound, a phosphite compound of the following formula (5) may, for example, be mentioned:

$$P(OR_1)(OR_2)(OR_3) \quad (5)$$

wherein each of $R_1$, $R_2$ and $R_3$ which are independent of one another, is an organic group, provided that at least one of them is a substituted phenyl group of the following formula (6):

wherein $R_4$ is a group of the formula $C(R_9)(R_{10})(R_{11})$ or an aryl group which may have a substituent, wherein each of $R_9$, $R_{10}$ and $R_{11}$ which may be the same or different from one another, is a hydrogen atom, a hydrocarbon group or a fluorinated hydrocarbon group, and each of $R_5$, $R_6$, $R_7$ and $R_8$ which may be the same or different, is a hydrogen atom or an organic group.

Preferred is the one wherein $R_4$ in the formula (6) has a steric hindrance greater than an isopropyl group as a whole. Specific examples of such a compound include diphenyl(2, 4-di-t-butylphenyl)phosphite, diphenyl(2-isopropylphenyl) phosphite and bis(2-t-butyl-4-methylphenyl) phenylphosphite.

Among them, preferred is a compound of the formula (5) wherein all of $R_1$, $R_2$ and $R_3$ are substituted phenyl groups of the formula (6). Specific examples of such a compound include tris(2,4-di-t-butylphenyl)phosphite, tris(2-t-butyl-4-methylphenyl)phosphite, tris(2-t-butyl-4-methoxyphenyl) phosphite, tris(o-phenylphenyl)phosphite, and tris(o-methylphenyl)phosphite.

As another preferred example of a non-cyclic phosphite compound, a phosphite compound of the following formula may, for example, be mentioned.

Namely, a phosphite compound of the formula (5) wherein at least one of $R_1$, $R_2$ and $R_3$ is a substituted 2-naphthyl group of the formula (7) may, for example, be mentioned:

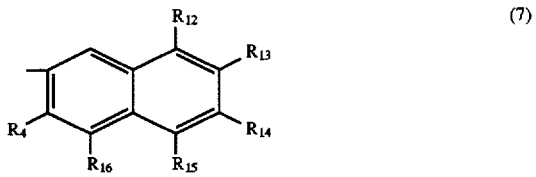

(7)

wherein $R_4$ is a group of the formula $C(R_9)(R_{10})(R_{11})$ or an aryl group which may have a substituent, wherein each of $R_9$, $R_{10}$ and $R_{11}$ which may be the same or different, is a hydrogen atom, a hydrocarbon group or a fluorinated hydrocarbon group, and each of $R_{12}$, $R_{13}$, $R_{14}$, $R_{15}$ and $R_{16}$ which may be the same or different, is a hydrogen atom or an organic group.

Preferred is the one wherein $R_4$ in the formula (7) has a steric hindrance greater than an isopropyl group as a whole. A specific example of such a compound may be diphenyl (3,6-di-t-butyl-2-naphthyl)phosphite.

More preferred is a compound of the formula (5) wherein each of $R_1$, $R_2$ and $R_3$ which may be the same or different is a 2-naphthyl group which may be substituted, and substituent $R_4$ on at least one 2-naphthyl group for $R_1$, $R_2$ and $R_3$ is as defined by the above formula (7). A specific example of such a compound may be bis(2-naphthyl)(3,6-di-t-butyl-2-naphthyl)phosphite.

Further preferred is a compound of the formula (5) wherein at least one of $R_1$, $R_2$ and $R_3$ is a substituted-2-naphthyl group of the formula (7), and the rest is a substituted phenyl group of the formula (6). Specific examples of such a compound include bis(3,6-di-t-butyl-2-naphthyl)(2,4-di-t-butylphenyl)phosphite, and bis(3,6-di-t-butyl-2-naphthyl)(2-t-butylphenyl)phosphite.

Most preferred is a compound of the formula (5) wherein all of $R_1$, $R_2$ and $R_3$ are substituted-2-naphthyl groups of the formula (7). Specific examples of such a compound include tris(3,6-di-t-butyl-2-naphthyl)phosphite, and tris(3,6-di-t-amyl-2-naphthyl)phosphite.

Another example of a preferred ligand is a phosphite compound of the formula (5) wherein each of $R_1$ and $R_2$ is a 2-naphthyl group which is substituted by hydrocarbon groups which may be the same or different at least at its 3-, 6- and 8-positions and which may have another substituents, and $R_3$ is an alkyl group, a cycloalkyl group or a phenyl group which may have a substituent only at the m-position and/or p-position. Specific examples of such a compound include bis(3,6,8-tri-t-butyl-2-naphthyl)phenylphosphite, and bis(3,6,8-tri-t-butyl-2-naphthyl)(p-tolyl)phosphite.

Among non-cyclic phosphite compounds as the phosphite compound useful for the present invention, another example of a preferred compound may be a bisphosphite or polyphosphite compound of the following formula (8):

(8)

wherein each of $R_{17}$ and $R_{18}$ which may be the same or different, is an aromatic hydrocarbon group, provided that at least one of the aromatic hydrocarbon groups has a hydrocarbon group on a carbon atom adjacent to the carbon atom bonded to an oxygen atom, $A_1$ is a n-valent organic group containing a partial structure of an aliphatic, alicyclic or aromatic hydrocarbon which may have a substituent, the respective [—O—P($OR_{17}$)($OR_{18}$)] groups may be the same or different, and n is an integer of from 2 to 4.

It is preferred to employ a phosphite compound of the formula (8) wherein at least one of $R_{17}$ and $R_{18}$ is a substituted phenyl group of the above formula (6), or a substituted 2-naphthyl group of the above formula (7).

It is more preferred to employ a phosphite compound of the formula (8) wherein each of $R_{17}$ and $R_{18}$ is a substituted phenyl group of the above formula (6). Specific examples of such a compound include compounds of the following formulas:

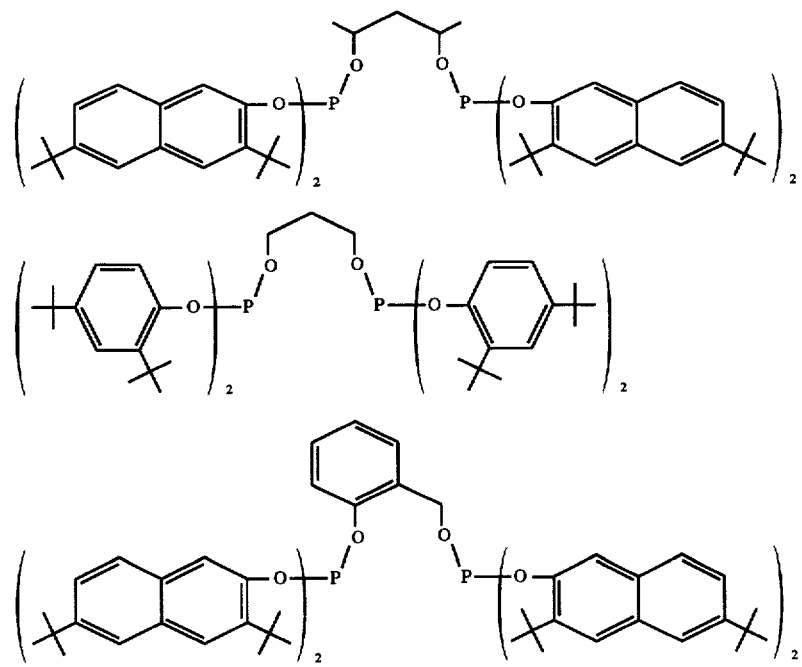

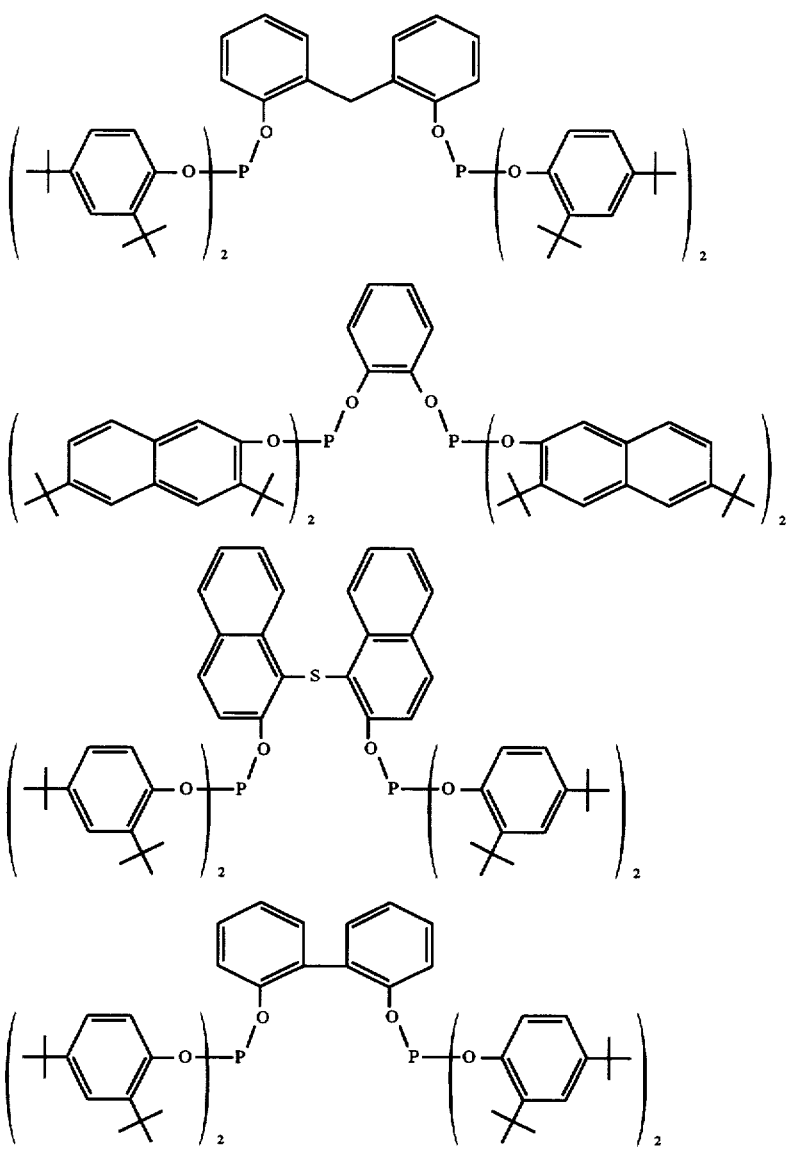

As another group of compounds among the phosphite compounds useful in the present invention, the cyclic phosphite compounds having a cyclic structure containing a phosphorus atom in their molecules, phosphite compounds of the following formula (9) may, for example, be:

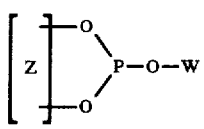

(9)

wherein Z is a bivalent organic group, and W is a substituted or unsubstituted monovalent hydrocarbon group.

As a typical organic group for Z in the formula (9), a bivalent aliphatic group or a bivalent aromatic group may, for example, be mentioned. The bivalent aliphatic group may, for example, be an alkylene group, an alkyleneoxyalkylene group, an alkylene-NX-alkylene group (wherein X is hydrogen or a monovalent hydrocarbon group), an alkylene-S-alkylene group or a cycloalkylene group. The bivalent aromatic group may, for example, be an arylene group, a biarylene group, an arylenealkylene group, an arylenealkylenearylene group, an aryleneoxyarylene group, an aryleneoxyalkylene group, an arylene-NX-arylene group, an arylene-NX-alkylene group (X is hydrogen or a monovalent hydrocarbon group), an arylene-S-alkylene group, and an arylene-S-arylene group.

Among these phosphite compounds, an example of a preferred compound may be a bicyclic or polycyclic phosphite compound containing a trivalent organic group Z' as shown by the following formula (10), just like a combination of a bivalent organic group Z and a monovalent hydrocarbon group W in the formula (9).

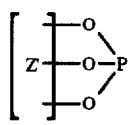

(10)

Specific examples of such a compound include 4-methyl-2, 6,7-trioxa-1-phosphabicyclo[2.2.2]octane, 4-ethyl-2,6,7-trioxa-1-phosphabicyclo[2.2.2]octane, 4-ethoxymethyl-2,6, 7-trioxa-1-phosphabicyclo[2.2.2]octane, and 4-acetoxymethyl-2,6,7-trioxa-1-phosphabicyclo[2.2.2] octane.

Another example of a preferred phosphite compound among compounds of the formula (9) may be a phosphite compound of the following formula (11):

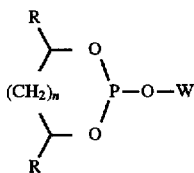
(11)

wherein each R is hydrogen, an alkyl group or a cycloalkyl group, which may have a substituent, and two R may be the same or different from each other, and n is an integer of from 0 to 4.

R in the formula (11) may, for example, be a methyl group, an ethyl group, a phenyl group, a tolyl group, a benzyl group, a naphthyl group, a hydroxymethyl group, a hydroxyethyl group, or a trifluoromethyl group.

It is preferred to employ a phosphite compound of the formula (9) wherein W is an aryl group having a hydrocarbon group on a carbon atom adjacent to the carbon atom bonded to an oxygen atom, as represented by the formula (6) or (7).

Another example of a preferred phosphite compound may be a phosphite compound of the following formula (12):

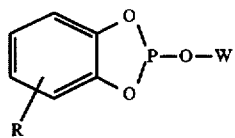
(12)

wherein W is a substituted or unsubstituted monovalent hydrocarbon group, R is a hydrocarbon group which may be substituted at an optional position, and R may form a condensed aromatic ring which is condensed with the phenyl ring.

R in the formula (12) may, for example, be an alkyl group, a cycloalkyl group, an alkoxy group, an acyl group, an acyloxy group or an aryl group which may have a substituent, or R is a condensed aromatic ring such as a naphthyl ring condensed with the phenyl ring.

It is more preferred to employ a phosphite compound of the formula (12) wherein W is an aryl group having a hydrocarbon group on a carbon atom adjacent to the carbon atom bonded to an oxygen atom, as shown by the formula (6) or (7).

Another example of a preferred phosphite among compounds of the formula (9) may be a phosphite compound of the following formula (13):

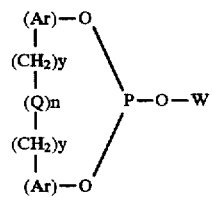
(13)

wherein each of two Ar which may be the same or different, is a substituted or unsubstituted arylene group, y is 0 or 1, Q is a bivalent group selected from the group consisting of $CR_{19}R_{20}$, O, S, $NR_{21}$, $SiR_{22}R_{23}$ and CO (wherein each of $R_{19}$ and $R_{20}$ O is a hydrogen atom, a $C_{1-12}$ alkyl group, a phenyl group, a tolyl group or an anisyl group, and each of $R_{21}$, $R_{22}$ and $R_{23}$ is hydrogen or a methyl group), and n is 0 or 1.

A more preferred phosphite compound among compounds of the formula (9) may, for example, be a phosphite compound of the following formula (14) or (15):

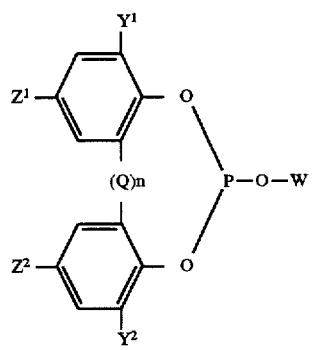
(14)

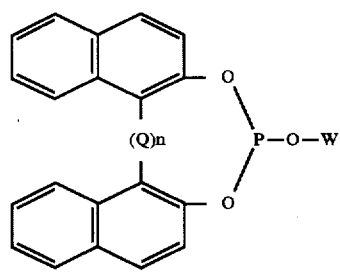
(15)

wherein Q is $CR_{24}R_{25}$, wherein each of $R_{24}R_{25}$ is hydrogen or an alkyl group, W is a substituted or unsubstituted $C_{1-18}$ alkyl group or an aryl group such as a phenyl group or a naphthyl group, which may have a substituent, each of $Z^1$, $Z^2$, $Y^1$ and $Y^2$ is a group selected from the group consisting of hydrogen, $C_{1-8}$ alkyl, aryl, alkaryl, aralkyl, an alicyclic group, a hydroxyl group and an oxy group. Specific examples of such a compound include the following compounds:

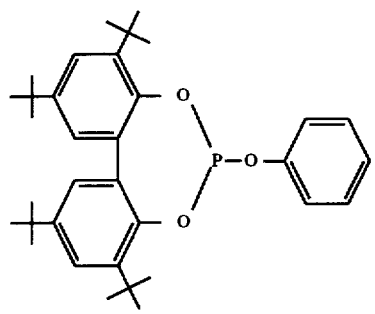

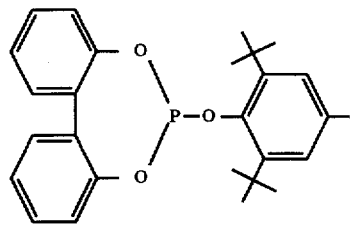

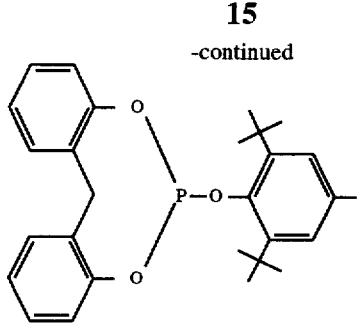
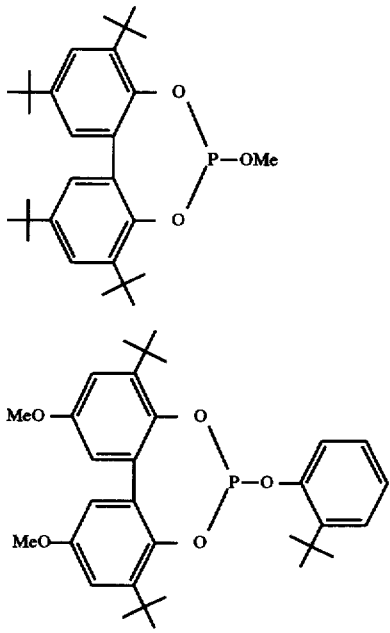

wherein a plurality of Z which may be the same or different, are bivalent organic groups, W is a substituted or unsubstituted m-valent hydrocarbon group, and m is from 2 to 6.

A preferred phosphite compound may, for example, be a phosphite compound of the following formula (17), i.e. a compound of the formula (16) wherein Z is as defined in the above formula (11), (12) or (13), or the respective Z are represented by a combination of such above-mentioned formulas.

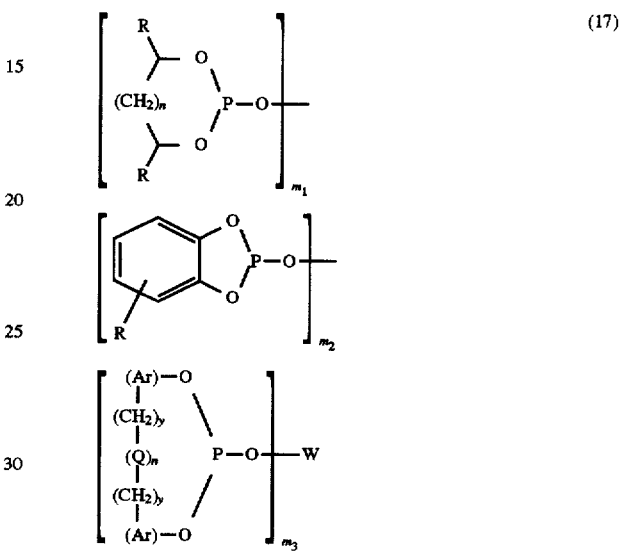

(17)

As another example of a cyclic phosphite compound among phosphite compounds useful in the present invention, a bisphosphite or polyphosphite compound of the following formula (16) may be mentioned.

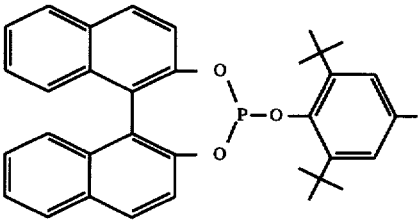

(16)

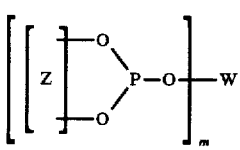

wherein each substituent is as defined in the above-mentioned formula (11), (12) and (13), the respective Z may be the same or different, W is a substituted or unsubstituted m-valent hydrocarbon group, and each of R groups which are independent of one another, is a group selected from the group consisting of substituted and unsubstituted monovalent hydrocarbon groups such as alkyl, aryl, alkaryl, aralkyl and alicyclic groups, each of $m_1$, $m_2$ and $m_3$ is from 0 to 6, provided that $m_1+m_2+m_3$ is from 2 to 6, and m is equal to $m_1+m_2+m_3$.

A more preferred phosphite compound is a phosphite compound of the formula (16) wherein Z is as defined in the above formula (13).

A still more preferred phosphite compound may, for example, be a phosphite compound of the formula (16) wherein Z is as defined in the above formula (14) and/or (15). Specific examples of such a compound include the following compounds:

17  18
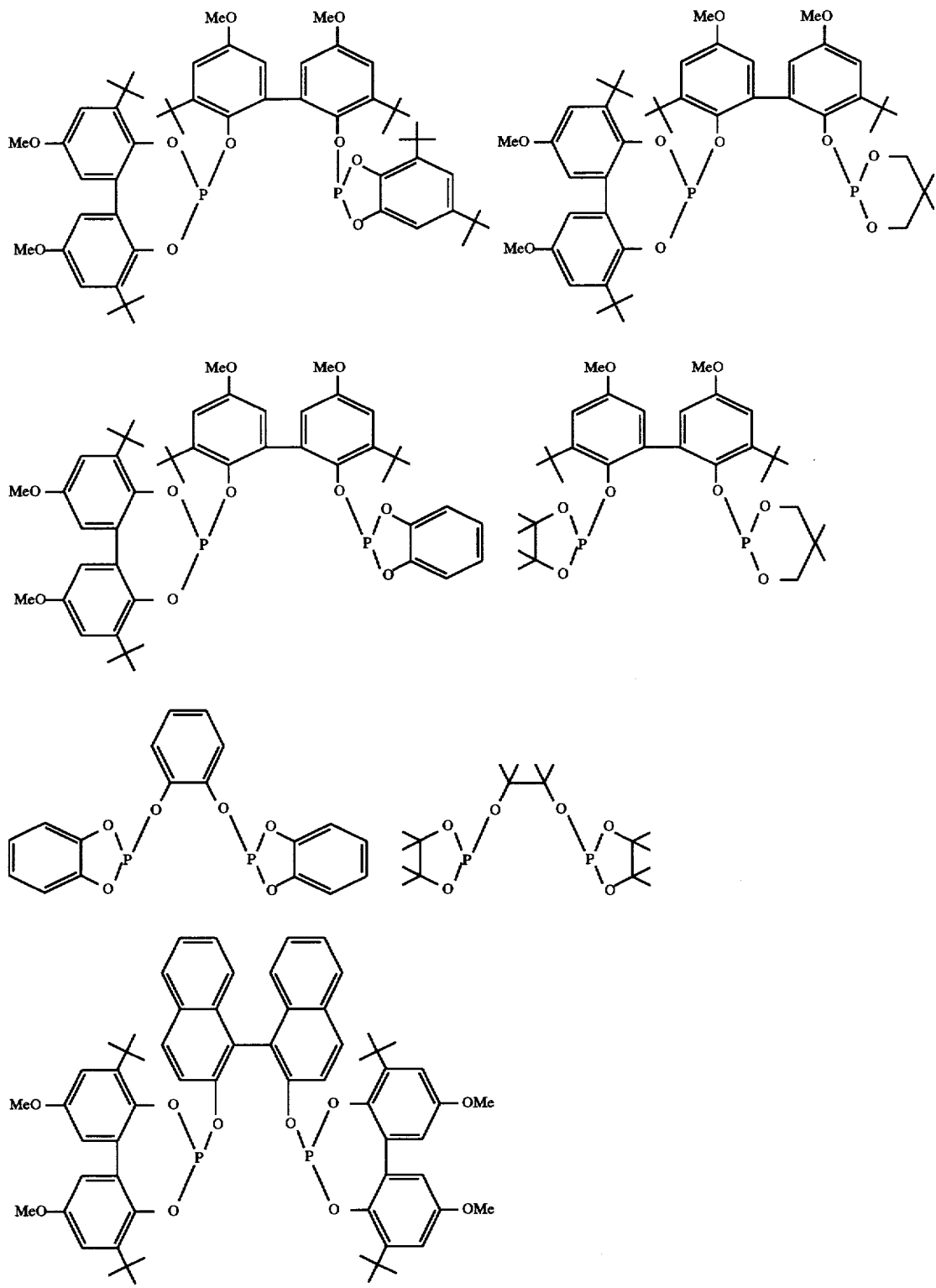

-continued
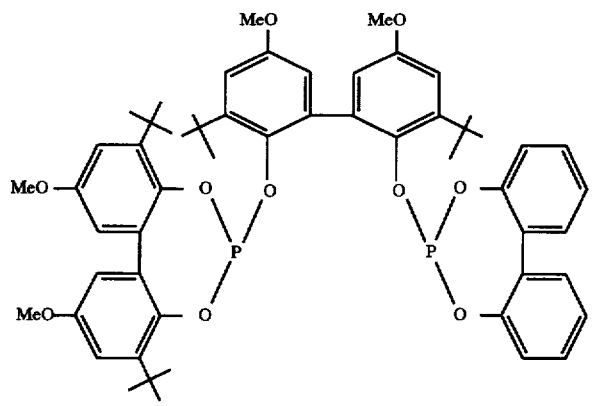
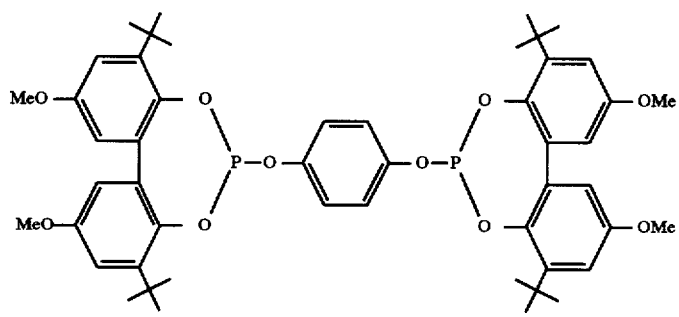
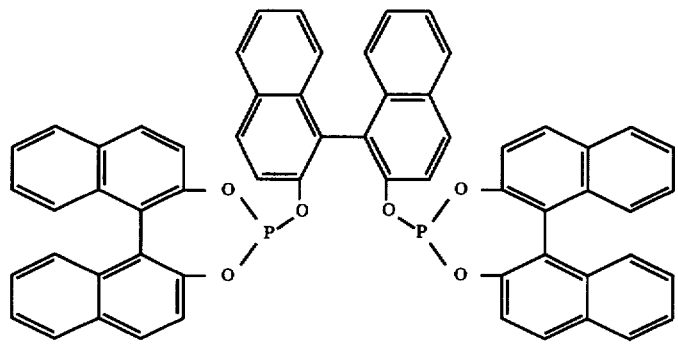
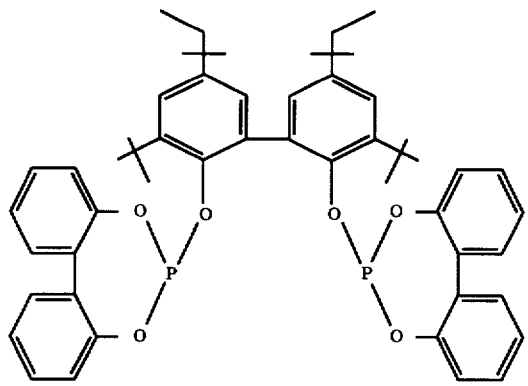

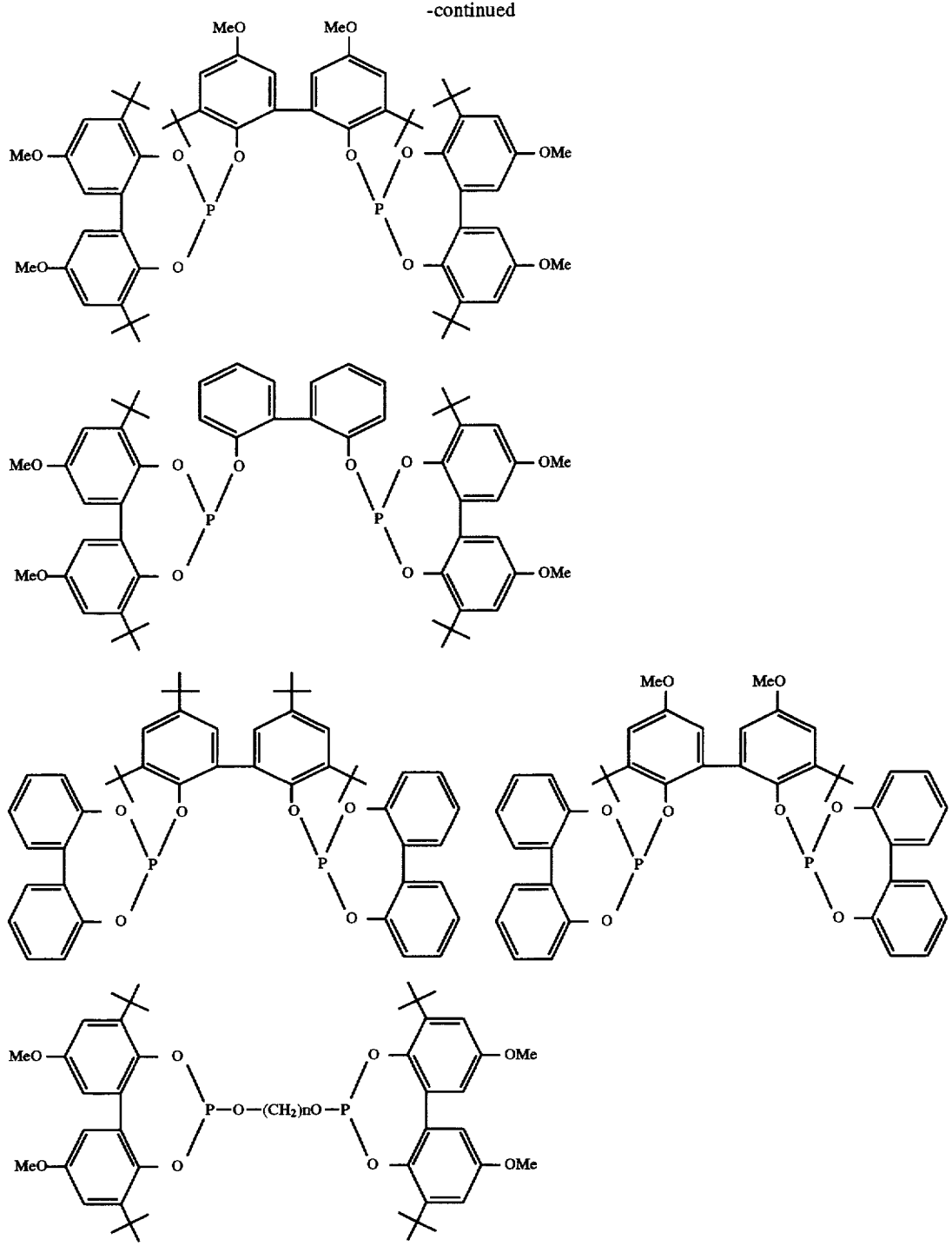
Among phosphite compounds useful in the present invention, a tricyclic polyphosphite having a cyclic structure containing a phosphorus atom in its molecule may, for example, be a phosphite compound of the following formula (18):
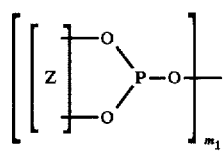
(18)

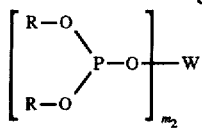

wherein W is a substituted or unsubstituted m-valent hydrocarbon group, Z is a bivalent organic group like in the formula (9), the plurality of Z may be the same or different from one another, each R is a substituted or unsubstituted monovalent hydrocarbon group, and each of $m_1$ and $m_2$ is from 1 to 6, provided that $m_1+m_2$ is 2 to 6, and m is equal to $m_1+m_2$.

A preferred phosphite compound is a phosphite compound of the formula (18) wherein Z is as defined in the above formula (11), (12) or (13), or the plurality of Z are represented by a combination of such above-mentioned formulas.

A more preferred phosphite compound may be a phosphite compound of the following formula (19) or (20) i.e. a compound of the formula (18) wherein Z is as defined in the above formula (14) or (15), or the plurality of Z are a combination of such above-mentioned formulas.

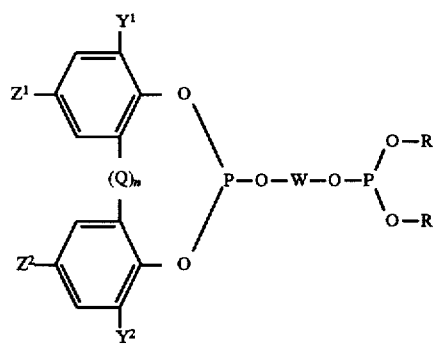

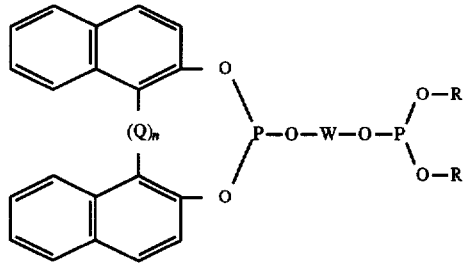

wherein X is a substituted or unsubstituted bivalent hydrocarbon group selected from the group consisting of alkylene, arylene and arylene-$(CH_2)_2$—$(Q)_n$—$(CH_2)_2$-arylene-(each arylene group may have a substituent), Q is a bivalent group selected from the group consisting of $CR_{26}R_{27}$, O, S, $NR_{28}$, $SiR_{29}R_{30}$ and CO (wherein each of $R_{26}$ and $R_{27}$ is hydrogen or an alkyl group, and each of $R_{28}$, $R_{29}$ and $R_{30}$ is hydrogen or a methyl group), and n is 0 or 1, and R is a substituted or unsubstituted hydrocarbon group such as an an alkyl group, an aryl group, an alkaryl group, an aralkyl group or an alicyclic group. Specific examples of such a compound include the following compounds:

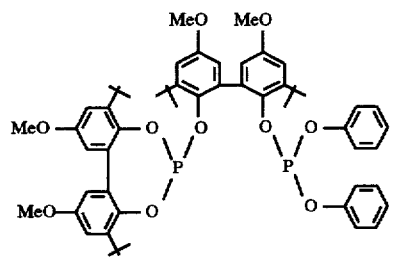

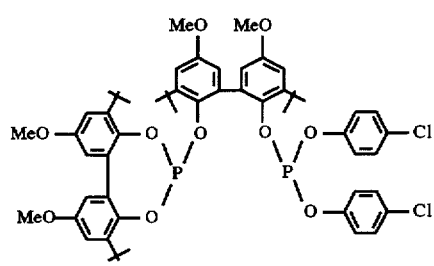

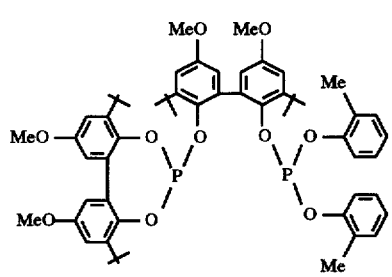

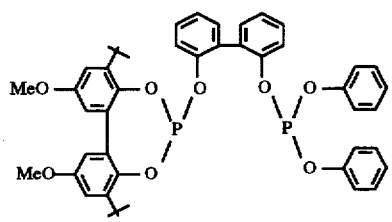

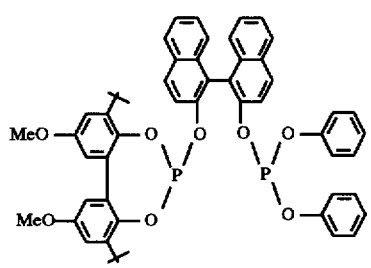

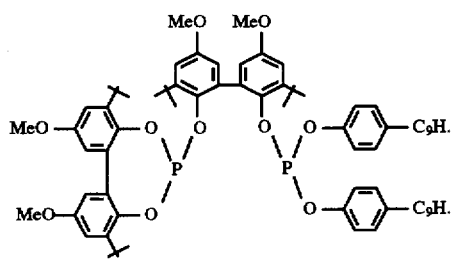

-continued

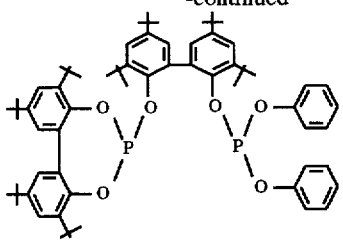

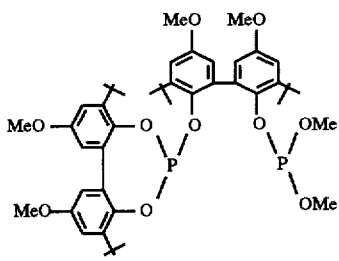

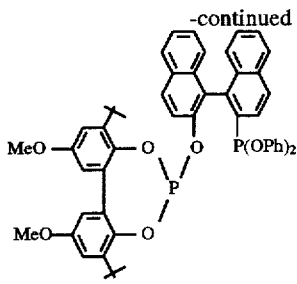

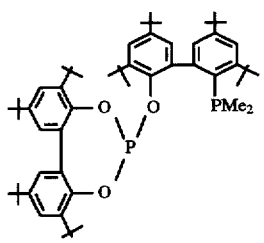

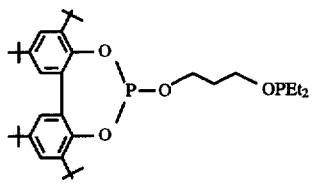

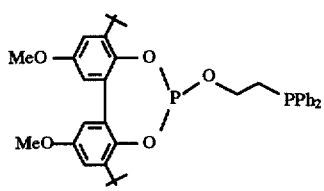

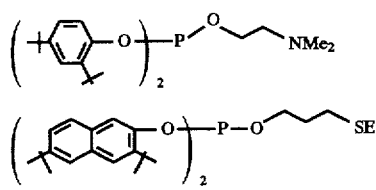

As a phosphite compound to be used in the present invention, a compound may be employed which has a phosphite structure as a partial structure and a partial structure having a coordinating ability such as a phosphine structure in the same molecule.

The partial structure having a coordinate ability may be the one having an unpaired electron pair such as —$PR_{31}R_{32}$, —$OPR_{31}R_{32}$, —$P(O)(OR_{31})$, —$NR_{31}R_{32}$, —$NR_{31}C(O)R_{32}$ or —$SR_{31}$, wherein $R_{26}$ and $R_{27}$ which may be the same or different is hydrogen or a monovalent hydrocarbon group, or $R_{31}$ and $R_{32}$ together form a ring structure.

Preferred among them is a phosphite compound which has the above-mentioned partial structure having a coordinating ability, as $R_1$, $R_2$ or $R_3$ in the above-mentioned formula (5), as $A_1$ in the above-mentioned formula (8), or as the substituent for W in the above-mentioned formula (9), (16) or (18). Specific examples of such a phosphite compound include the following compounds:

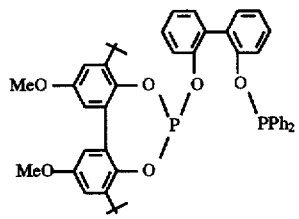

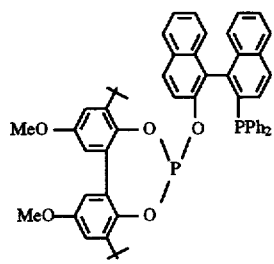

Among the above-mentioned phosphite compounds, the non-cyclic phosphite compounds having no ring structure containing a phosphorus atom in their molecules are highly decomposable in the liquid recycling process, as compared with cyclic phosphites. On the other hand, it is also known that as described above, if compounds such as phosphonic acid formed by the decomposition of a phosphite ligand are present, decomposition of the ligand will further be promoted.

The present inventors have found that in a process for separating an aldehyde product or high boiling substances from a reaction product solution obtained by a hydroformylation reaction, it is possible to suppress the loss of a non-cyclic phosphite ligand which used to be regarded as highly decomposable, by the presence of an amine, even if compounds such as phosphonic acid which promote the decomposition of the ligand are present. Further, they have found that also in a case where steam distillation is employed as the separating operation, the above-mentioned loss of a non-cyclic phosphite ligand can effectively be suppressed by the presence of an amine.

Namely, in a separating operation for separating, from a reaction product solution obtained by a hydroformylation reaction in the presence of a rhodium complex catalyst having a non-cyclic phosphite compound as a ligand, at least one component selected from the group consisting of an unreacted olefinic unsaturated compound, the aldehyde product, a solvent, a medium-boiling by-product and a high-boiling by-product, it is possible to suppress the loss of the non-cyclic phosphite ligand, formation of by-products and decrease of the reaction activity to the minimum levels, by the presence of an amine, even if compounds such as phosphonic acid which promote the decomposition of the ligand are present.

The amine to be present is not particularly limited. Specifically, it may, for example, be a primary amine such as ethylamine, propylamine or butylamine, a secondary amine such as diethylamine, dipropylamine or dibutylamine, a tertiary amine such as triethylamine, trioctylamine or dimethyllaurylamine, an aromatic amine such as styreneamine or diphenylamine, an alicyclic amine such as cyclohexylamine, a diamine such as ethylenediamine or propylenediamine, an alkanolamine such as ethanolamine, diethanolamine or glycolamine, or a heterocyclic amine such as pyridine.

Among the above amines, a tertiary amine is preferred. Examples of a preferred tertiary amine includes triethylamine, tri-n-butylamine, trioctylamine, tridecylamine, tridodecylamine, dimethyllaurylamine, N,N-di-n-butyl-2-ethylhexylamine, N,N-diisobutyl-2-ethylhexylamine, N-propyl-N-butyl-n-butylamine, N-propyl-N-butyl-2-ethylhexylamine, dimethyldecylamine, dimethyldodecylamine and dimethyltetradecylamine.

In an industrial hydroformylation process, it is common to conduct separation of the aldehyde product and the catalyst by distillation. In such a case, the added amine should better be separated on the catalyst solution side rather than distilled on the aldehyde product side. Accordingly, the amine to be used preferably has a boiling point higher than the aldehyde product, and an amine having a relatively large number of carbon atoms is preferred.

The amount of the amine is usually within a range of form 0.1 to 100 mols, preferably from 1 to 20 mols, per mol of rhodium in the catalyst solution. The amine may be added to the hydroformylation reaction step or to a step between the respective separating operations. In the present invention, it is sufficient to maintain a condition such that the above-mentioned amount of an amine is present in the above-mentioned separating operation. In the present invention, it is particularly preferred to add the amine at the time of the above-mentioned separating operation, since such is particularly effective for suppressing the decomposition of the phosphite ligand.

On the other hand, as the rhodium source for the rhodium-phosphite complex catalyst, a rhodium complex such as rhodium acetylacetonate or [Rh(COD)(OAc)]$_2$, an organic salt such as rhodium acetate, an inorganic salt such as rhodium nitrate, an oxide such as rhodium oxide may, for example, be used (wherein COD represents cyclooctadiene, and Ac represents an acetyl group).

The rhodium source may be supplied directly to the hydroformylation reactor. Otherwise, it may be reacted together with carbon monoxide, hydrogen and a phosphite compound in a solvent under a high temperature and pressure condition outside the reactor to prepare a rhodium complex catalyst beforehand. The solvent to be used for the preparation of the catalyst is usually selected among the solvents for reaction as described hereinafter, but it may not necessarily be the same solvent as the solvent for reaction. The preparation is conducted usually under a pressure of from atmospheric pressure to 10 kg/cm$_2$G at a temperature of from room temperature to 150° C.

A free phosphite ligand present in the hydroformylation process employed in the present invention, may be present in any excess amount. For example, it is usually at least 1 mol per mol of rhodium present in the reaction medium, and it may be present up to 100 mols or even more. In general, the sum of the (complex forming) phosphite bonded to rhodium and the free (non-complex forming) phosphite present in the reaction medium may be from about 4 to about 500 mols per mol of rhodium for most purposes. Further, to maintain a predetermined amount of free ligand in the reaction medium, a supplemental phosphite ligand may be supplied to the reaction medium in an optional manner. It is usual to employ a ligand of the same type for both the free phosphite ligand and the phosphite ligand for the rhodium-phosphite complex catalyst. However, if necessary, different phosphite ligands may be used for the respective purposes, or a mixture of two or more different phosphite ligands may be used.

The amount of the rhodium-phosphite complex catalyst present in the reaction medium for the hydroformylation process of the present invention may be the minimum amount required to bring about a predetermined rhodium concentration to be employed and may be at least an amount satisfying the standard relating to a catalytic amount of rhodium. The rhodium concentration in the hydroformylation reaction medium is usually sufficient at a level within a range of from 1 ppm to 1000 ppm, as calculated as metal rhodium, and it is preferred to employ a rhodium concentration of from 10 to 500 ppm, more preferably from 25 to 350 ppm.

The olefinic unsaturated compound to be used in the present invention may be a single substance or a mixture, and it may have a straight chain, branched chain or cyclic structure. A preferred olefinic unsaturated compound is a $C_{2-20}$ olefin, which may contain two or more ethylenically unsaturated groups. It may contain a carbonyl group, a carbonyloxy group, an oxy group, a hydroxyl group, an oxycarbonyl group, a halogen atom, an alkoxy group, an aryl group, an alkyl group or a haloalkyl group which presents substantially no adverse effect to the hydroformylation reaction.

The olefinic unsaturated compound includes, for example, an α-olefin, an internal olefin, an alkylalkenoic acid, an alkenylalkanoic acid, an alkenylalkyl ether and an alkenol. Specifically, it includes, for example, ethylene, propylene, butene, pentene, hexene, octene, nonene, decene, dodecene, octadecene, cyclohexene, a mixture of propylene dimers, a mixture of propylene trimers, a mixture of propylene tetramers, a mixture of butene dimers, a mixture of butene trimers, styrene, 3-phenyl-1-propene, 1,4-hexadiene, 1,7-octadiene, 3-cyclohexyl-1-butene, allyl alcohol, 1-hexen-4-ol, 1-octen-4-ol, vinyl acetate, allyl acetate, 3-butenyl acetate, allyl propionate, allyl acetate, methyl methacrylate, 3-butenyl acetate, vinyl ethyl ether, vinyl methyl ether, allyl ethyl ether, n-propyl-7-octenoate, 3-butenenitrile, and 5-hexeneamide. As the solvent for the hydroformylation reaction, the feed olefin itself may be used, or a mixture of two or more solvents may be employed. Usually, it is preferred to employ the aldehyde product and/or a high boiling aldehyde liquid condensation by-product formed in the reaction system. For example, even when an optional primary solvent is employed at the initial stage of a continuous process, by the nature of the continuous process, the primary solvent usually finally becomes to be composed of the aldehyde product and a high boiling aldehyde liquid condensation by-product. If desired, such an aldehyde condensation by-product may preliminarily be formed. The amount of the solvent is not critical to the present invention, and the solvent may be in an amount sufficient to maintain a specific rhodium concentration desired for the predetermined process and to perform the role as the reaction medium. The amount of the solvent is usually from about 5 to about 95 wt %, based on the total weight of the reaction medium.

As a hydroformylation reaction condition, it is preferred to operate the hydroformylation process under total gas pressure of hydrogen, carbon monoxide and the olefinic unsaturated compound of less than 500 kg/cm$_2$G, more preferably less than 200 kg/cm$_2$G. The lower limit of the total gas pressure is defined by the amounts of the reactants necessary to accomplish the initial rate of the reaction. Further, the carbon monoxide partial pressure in the hydroformylation reaction of the present intention is preferably from 0.1 to 100 kg/cm$^2$, more preferably from 1 to 7 kg/cm$^2$, and the hydrogen partial pressure is preferably from 0.1 to 100 kg/cm$^2$, more preferably from 1 to 8 kg/cm$^2$. In general, the molar ratio of hydrogen to carbon monoxide gas (H$_2$:CO) is from 1:10 to 100:1, preferably from 1:1 to 10:1. The reaction can usually be carried out at a temperature of from room temperature to 150° C., and a reaction temperature within a range of from 50° to 120° C. is preferred for most of the olefin starting materials. At a reaction temperature substantially exceeding 120° C., no substantial merit will be observed, and a deterioration of the catalytic activities is expected as disclosed in Japanese PCT Publication No. 501268/1986, such being usually undesirable.

The hydroformylation reaction of an olefin is usually carried out under the above-mentioned hydroformylation reaction conditions by continuously supplying an olefinic unsaturated compound as starting material, oxo gas and a catalyst solution to a continuous type reactor.

A medium-boiling by-catalyst formed by the above hydroformylation reaction means a compound having a lower boiling point than the organophosphorus compound, and it is formed mainly by a secondary side reaction of aldehyde formed by the hydroformylation reaction. For example, in a hydroformylation reaction of propylene, straight chain n-butyraldehyde and branched chain isobutyraldehyde will be formed. These aldehyde products are highly reactive and tend to undergo polymerization or condensation slowly in the presence of the catalyst even at a relatively low temperature, to form medium-boiling polycondensation products.

Such medium-boiling polycondensation products may be, in the case of n-butyraldehyde, a dimer and a trimer as its self polymerization product, 2-ethylhexenal as a condensed dimer, and 2-ethylhexenal and 2-ethylhexanol as its hydrogenation products, n-butanol as a hydrogenated product of n-butyraldehyde, or dibutylacetal of n-butyraldehyde. Further, also from isobutyraldehyde, the dimer and trimer will be formed as self condensed products by reactions similar to those of n-butyraldehyde. Furthermore, interpolymerization products of n-butyraldehyde and isobutyraldehyde, a dimer, a trimer and derivatives thereof will be formed.

In the hydroformylation reaction, in addition to the above medium-boiling by-product, a high-boiling by-product having a boiling point higher than the organic phosphorus compound will be formed by side reactions.

Now, the present invention will be described in further detail with reference to Examples and Comparative Examples. However, it should be understood that the present invention is by no means restricted to such specific Examples.

The present applicant has devised an accelerated phosphite loss test method to prove that in a continuous liquid recycling hydroformylation process using a rhodium-phosphite complex catalyst, the conditions for separating the aldehyde product are influential over suppression of decomposition of the phosphite to the minimum level. This method consists of permitting a rhodium-phosphite complex catalyst solution to be present under a far severer condition than normally experienced in the separation of the aldehyde product, etc., in a practical process, to obtain a useful result in a short period of time. For example, the loss rate of the phosphite ligand is usually at a level of a few percent per day, and it takes a number of days for quantitative analysis by a standard aldehyde separating method. Whereas, the accelerated phosphite loss test method by the present applicant can be completed in a few hours by continuously maintaining the catalyst solution at the temperature for separating aldehyde in the absence of carbon monoxide and hydrogen (oxo gas). In some of the following Examples, this accelerated phosphite loss test method was employed to evaluate the stability of the catalyst.

EXAMPLE 1

A continuous hydroformylation reaction was carried out by reacting mixed octene obtained by dimerization of butene (hereinafter referred to as mixed octene) with carbon monoxide and hydrogen to form nonylaldehyde, in the presence of free phosphite and a rhodium complex catalyst consisting essentially of rhodium complexed with a phosphite of the following formula [tris(3,6-di-t-butyl-2-naphthyl)phosphite: hereinafter referred to as DBNO]. The hydroformylation conditions were such that the Rh concentration was 50 mg/l, the molar ratio of the phosphite/Rh was 10, the reaction temperature was 130° C., and the reaction pressure was 50 kg/cm$_2$G. The hydroformylation reaction product solution was charged to a 500 ml distillation flask equipped with a condenser and connected to a vacuum pump, and then the pressure in the flask was gradually lowered to about 40 mmHg. Then, the reaction product solution was continuously distilled under heating at a temperature of about 90° C., and after distilling unreacted octene and the majority of nonylaldehyde off, the distillation residue was analyzed. The results are shown in Table 1.

TABLE 1

| Temp. (°C.) | Residence time (hr) | Value P in the formula (1) | Formation rate (%) of by-product |
|---|---|---|---|
| Example 1 | 90 | 1.0 | 0.310 | 0 |

EXAMPLES 2 TO 5 AND COMPARATIVE EXAMPLES 1 TO 11

In Example 1, the hydroformylation reaction product solution was continuously distilled, and the reaction solution obtained as the distillation residue was subjected to steam distillation to distill nonylaldehyde off. The distillation conditions and the results are shown in Table 2.

TABLE 2

|  | Temp. (°C.) | Steam fraction | Residence time (hr) | Value P in the formula (3) | Decomposition rate (%) of ligand |
|---|---|---|---|---|---|
| Example 2 | 90 | 0.10 | 0.6 | 0.239 | 0 |
| Example 3 | 90 | 0.14 | 0.8 | 0.446 | 0 |
| Example 4 | 90 | 0.13 | 0.5 | 0.259 | 0 |
| Example 5 | 90 | 0.50 | 0.2 | 0.398 | 0 |
| Comparative Example 1 | 90 | 0.50 | 1.0 | 1.989 | 20 |
| Comparative Example 2 | 90 | 0.63 | 0.6 | 1.504 | 21 |
| Comparative Example 3 | 90 | 0.33 | 1.0 | 1.313 | 9 |
| Comparative Example 4 | 90 | 0.50 | 0.7 | 1.393 | 21 |
| Comparative Example 5 | 90 | 0.50 | 1.4 | 2.785 | 29 |
| Comparative Example 6 | 90 | 0.63 | 0.5 | 1.253 | 20 |
| Comparative Example 7 | 90 | 0.60 | 0.5 | 1.194 | 17 |
| Comparative Example 8 | 100 | 0.50 | 1.0 | 3.098 | 20 |
| Comparative Example 9 | 110 | 0.15 | 0.9 | 1.273 | 18 |
| Comparative Example 10 | 110 | 0.15 | 1.6 | 2.264 | 11 |
| Comparative Example 11 | 110 | 0.15 | 3.1 | 4.386 | 22 |

EXAMPLE 6

In a continuous catalyst liquid recycling system, a hydroformylation reaction of mixed octene was carried out. Then, the catalyst solution separated by distillation and steam distillation was recycled to the reactor.

Firstly, mixed octene, oxo gas and a rhodium-phosphite complex catalyst were supplied to a bubble tower-type reactor having a capacity of 6 l, and a hydroformylation reaction was carried out at a temperature of 120° C. under a pressure of 50 kg/cm$_2$G. As the phosphite compound, the same phosphite ligand (DBNO) as used in Example 1, was employed. The catalyst solution before initiating a recycling operation was the one having 1 g of Rh and 77 g of the above phosphite dissolved in 1 l of toluene. The mixed octene, the catalyst solution and the oxo gas were supplied to the reactor at rates of 1.6 l/hr, 80 ml/hr and 3.8 m$_3$/hr, respectively. The reaction solution was once stored in a receptor, subjected to oxo gas removal and then sent to a distillation column for recovering unreacted octene, whereby the unreacted octene and the catalyst solution containing the aldehyde product were separated and respectively collected in receptors. The catalyst solution containing the aldehyde product was sent to a steam distillation column, whereby the catalyst solution and the aldehyde product were separated. The separated catalyst solution was sent as a catalyst solution for recycling to the reactor instead of the catalyst solution supplied at the initiation of the reaction. On the other hand, the aldehyde product was collected in a separate receptor. The recycling operation was carried out in this manner, and when the seventh cycle was completed, the decomposition rate of the phosphite was 1.75%. The distillation conditions were as shown in Table 3.

TABLE 3

|  | Temp. (°C.) | Steam fraction | Residence time (hr) | Value P |
|---|---|---|---|---|
| Distillation column for recovering unreacted octene | 90 | — | 1.0 | 0.310 [Formula (1)] |
| Distillation column for recovering catalyst | 90 | 0.3 | 0.25 | 0.298 [Formula (3)] |

EXAMPLES 7 AND 8 AND COMPARATIVE EXAMPLES 12 TO 23

In the autoclave having a capacity of 0.5 l, a continuous hydroformylation reaction was carried out by reacting propylene with carbon monoxide and hydrogen to form butyraldehyde, in the presence of free phosphite and a rhodium complex catalyst consisting essentially of rhodium complexed with a phosphite ligand of the following formula (A or B). The hydroformylation conditions were such that the rhodium complex catalyst and the phosphite were dissolved in 30 ml of toluene so that the Rh concentration became 250 mg/l and the molar ratio of the phosphite/Rh became 4, and the reaction was carried out substantially to the very end at a reaction temperature of 90° C. under a reaction pressure of 7 kg/cm$_2$G. From the reaction product solution obtained by this hydroformylation reaction, aldehyde was distilled by batch distillation under a pressure of 200 mmHg at a bottom temperature of 77° C. using an Oldarshow type distillation apparatus (20 plates). The catalyst solution obtained as the distillation residue was charged into a 0.2 l autoclave and then subjected to heat treatment at a predetermined temperature. The results are shown in Table 4.

TABLE 4

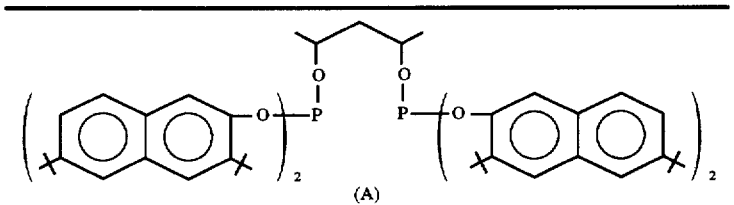
(A)

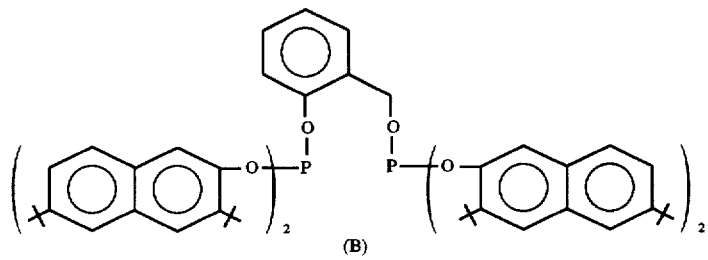
(B)

| | ligand | Temp. (°C.) | Residence time (hr) | Value P in the formula (1) | Decomposition rate (%) of ligand |
|---|---|---|---|---|---|
| Example 7 | A | 100 | 1.0 | 0.45 | 0.0 |
| Example 8 | B | 120 | 1.0 | 0.89 | 0.0 |
| Comparative Example 12 | A | 120 | 2.0 | 1.79 | 8.8 |
| Comparative Example 13 | A | 140 | 1.0 | 1.66 | 13.6 |
| Comparative Example 14 | A | 140 | 2.0 | 3.31 | 31.5 |
| Comparative Example 15 | A | 160 | 0.5 | 1.45 | 74.8 |
| Comparative Example 16 | A | 160 | 1.0 | 2.90 | 92.3 |
| Comparative Example 17 | A | 160 | 2.0 | 5.80 | 99.7 |
| Comparative Example 18 | B | 140 | 1.0 | 1.66 | 34.7 |
| Comparative Example 19 | B | 140 | 2.0 | 3.31 | 29.0 |
| Comparative Example 20 | B | 160 | 0.5 | 1.45 | 54.5 |
| Comparative Example 21 | B | 160 | 1.0 | 2.90 | 68.6 |
| Comparative Example 22 | B | 160 | 2.0 | 5.80 | 81.2 |
| Comparative Example 23 | B | 120 | 2.0 | 1.79 | 21.8 |

EXAMPLES 9 AND 10 AND COMPARATIVE EXAMPLES 24 TO 26

The heat treatment of the catalyst solution was carried out in the same manner as in Example 7 except that the hydroformylation reaction was conducted at a temperature of 70° C., and a phosphite of the following formula C was used as the phosphite ligand. The heat treating conditions and the results are shown in Table 5.

TABLE 5

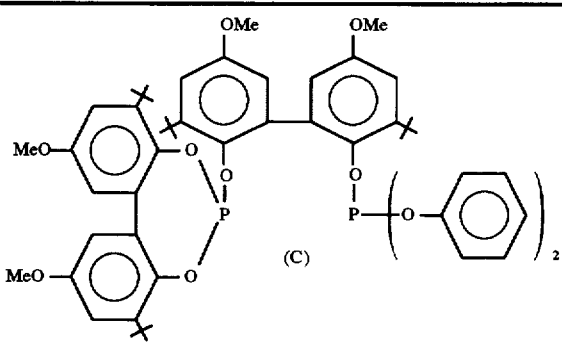

|  | Temp. (°C.) | Residence time (hr) | Value P in the formula (1) | Decomposition rate (%) of ligand |
|---|---|---|---|---|
| Example 9 | 120 | 0.5 | 0.45 | 1.0 |
| Example 10 | 120 | 1.0 | 0.63 | 2.4 |
| Comparative Example 24 | 120 | 2.0 | 1.79 | 10.6 |
| Comparative Example 25 | 160 | 0.5 | 1.45 | 8.2 |
| Comparative Example 26 | 160 | 2.0 | 5.80 | 32.5 |

EXAMPLES 11 TO 16

Using the same phosphite ligand (A or B) as used in Example 7, the rhodium complex catalyst and the phosphite were dissolved in a toluene solvent so that the Rh concentration became 250 mg/l and the molar ratio of the phosphite/Rh became 4. This catalyst solution was charged into a 0.2 l autoclave and then subjected to heat treatment at a predetermined temperature (accelerated phosphite loss test method). The results are shown in Table 6.

TABLE 6

| | ligand | Temp. (°C.) | Residence time (hr) | Value P in the formula (1) | Decomposition rate (%) of ligand |
|---|---|---|---|---|---|
| Example 11 | A | 90 | 1.0 | 0.31 | 0.0 |
| Example 12 | A | 90 | 2.0 | 0.63 | 0.0 |
| Example 13 | A | 90 | 3.0 | 0.94 | 0.0 |
| Example 14 | B | 90 | 1.0 | 0.31 | 0.0 |
| Example 15 | B | 90 | 2.0 | 0.63 | 0.0 |
| Example 16 | B | 90 | 3.0 | 0.94 | 0.0 |

From the results of Examples 2 to 16 and Comparative Examples 1 to 26, it is apparent that the phosphite ligands were not substantially decomposed by carrying out the separating operation under the specific conditions according to the present invention.

EXAMPLES 17 TO 25 AND COMPARATIVE EXAMPLES 27 TO 29

The following experiment was carried out to determine the effect of adding an amine in the separating operation.

$[Rh(COD)(OAc)]_2$ was dissolved in toluene so that the rhodium concentration became 250 mg/l, and a phosphite compound of the following formula (B) was added in an amount of 4 mols per mol of rhodium to obtain a catalyst solution. Using this catalyst solution, a hydroformylation reaction of propylene was carried out for 3 hours at a reaction temperature of 90° C. under an oxo gas pressure of 3 kg/cm$_2$G. The hydroformylation reaction product solution was continuously distilled under a pressure of 250 mmHg at a bottom temperature of 80° C. by means of an Oldarshow type distillation column of 20 plates, to separate the aldehyde product and the catalyst solution. This catalyst solution was charged into an induction stirring type autoclave and treated at 90° C. for 8 hours in a sealed condition. The heat treated solution was further stored for 2 months at room temperature in a nitrogen atmosphere. Upon expiration of 2 months, the catalyst solution was analyzed, whereby the phosphite ligand (B) in the catalyst solution was found to have been all decomposed, and phosphonic acid was found to have been formed. To this catalyst solution, the same phosphite ligand (B) as used in the hydroformylation reaction was added in an amount of 4 mols per mol of rhodium (whereby the rhodium concentration in the liquid was 250 mg/l), and an additive as identified in Table 7 was further added thereto. The solution thereby obtained was charged into an induction stirring type autoclave and treated at 90° C. for 2 hours in a sealed condition. The value B in the formula (1) was 0.63 as calculated from the treating conditions. Then, the liquid was withdrawn, and then a quantitative analysis of the ligand was carried out by liquid chromatography. The type and the amount of the additive as well as the decomposition rate (%) of ligand are shown in Table 7.

TABLE 7

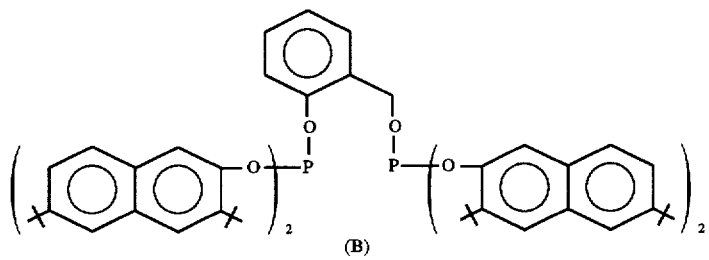

(B)

| | Additive | Amount[a] | Decomposition rate (%) of ligand |
|---|---|---|---|
| Example 17 | Trioctylamine | 1.0 | 15.9 |
| Example 18 | Trioctylamine | 10.0 | 10.3 |
| Example 19 | Trioctylamine | 20.0 | 3.0 |
| Example 20 | Trioctylamine | 50.0 | 3.6 |
| Example 21 | Trioctylamine | 100.1 | 4.4 |
| Example 22 | Tridodecylamine | 6.8 | 4.5 |
| Example 23 | Dimethyllaurylamine | 16.6 | 17.4 |
| Example 24 | N-Methylpyrrolidine | 35.7 | 25.4 |
| Example 25 | Diethanolamine | 34.7 | 27.8 |
| Comparative Example 27 | Nil | — | 71.6 |
| Comparative Example 28 | Phthalic anhydride | 4.3 | 82.3 |
| Comparative Example 29 | Catechol | 6.4 | 86.8 |

[a]: Molar ratio to the molar amount of rhodium.

From the results in Table 7, it is evident that in a catalyst solution wherein compounds such as phosphonic acid formed by the decomposition of ligand are present, decomposition of the non-cyclic phosphite ligand such as the one of the formula (B) is promoted (Comparative Examples 27 to 29), whereas the decomposition of the ligand is suppressed by an addition of an amine (Examples 17 to 25).

As mentioned in the background of the invention, the conventional knowledge relating to the conditions for separating operations for a phosphite type process was limited to the one relating to the temperatures. On the other hand, the decomposition rate of the phosphite under each separating operation condition is changeable continuously, and optimum operation conditions acceptable for industrial purposes are difficult to foresee. The present invention is based on a discovery that in a separating operation after the hydroformylation reaction, an interrelation defined by a specific formula of the temperature and the residence time, or the temperature, the residence time and the steam fraction, is important, and industrial operation conditions can be set without relying on any experiment.

Although the operation temperature may vary depending upon the type of the separating operation and the type of the aldehyde to be separated, according to the present invention, it is possible to set the optimum residence time at the operation temperature of each separating operation. This is particularly important in a continuous liquid catalyst recycling process.

Namely, by conducting a separating operation of a hydroformylation reaction product solution under the specific conditions of the present invention, it is possible to suppress the loss of the phosphite ligand and formation of by-products such as high boiling substances to the minimum levels, whereby aldehydes can be produced industrially advantageously in a liquid recycling process employing a phosphite ligand which shows high catalytic activities and excellent selectivity.

What is claimed is:

1. A method for producing aldehydes, which comprises reacting an olefinic unsaturated compound with carbon monoxide and hydrogen for hydroformylation in the presence of a rhodium-phosphite complex catalyst to obtain a reaction product solution containing the rhodium-phosphite complex catalyst and an aldehyde product, and separating from the reaction product solution at least one component selected from the group consisting of carbon monoxide, hydrogen, an unreacted olefinic unsaturated compound, the aldehyde product, a solvent, a medium-boiling by-product and a high-boiling by-product by a separating operation, wherein at least one separating operation is carried out substantially in the absence of water, and the temperature and the residence time in the separating operation are selected to be within such ranges that value P calculated from the following formula (1) would be at most 1:

$$P = 5.0 \times 10^3 \times \exp[-5000/(T_1+273)] \times \theta T_1 \quad (1)$$

where $T_1$ is the maximum temperature (°C.) in the separating operation, and $\theta T_1$ is the residence time (minutes) of the liquid in the separating operation.

2. The method for producing aldehydes according to claim 1, wherein the temperature and the residence time in the separating operation are selected to be within such ranges that value P calculated from the following formula (2) would be at most 1:

$$P = 9.6 \times 10^3 \times \exp[-5000/(T_1+273)] \times \theta T_1 \quad (2)$$

where $T_1$ is the maximum temperature (°C.) in the separating operation, and $\theta T_1$ is the residence time (minutes) of the liquid in the separating operation.

3. The method for producing aldehydes according to claim 1, wherein the separating operation is an operation for separating the unsaturated olefinic unsaturated compound or the aldehyde product by distillation.

4. The method for producing aldehydes according to claim 1, wherein the temperature $T_1$ in the separating operation is from 30° to 160° C., and the residence time $\theta T_1$ is from 0.01 to 180 minutes.

5. The method for producing aldehydes according to claim 1, wherein the ligand of the rhodium-phosphite complex catalyst is a cyclic or non-cyclic bisphosphite.

6. The method for producing aldehydes according to claim 1, wherein at least one alcohol component of the phosphite compound is an aromatic alcohol having a hydrocarbon substituent on a carbon atom adjacent to the carbon atom bonded to an oxygen atom.

7. The method for producing aldehydes according to claim 1, wherein the ligand of the rhodium-phosphite complex catalyst is a phosphite compound having no cyclic structure containing a phosphorus atom in its molecule.

8. The method for producing aldehydes according to claim 7, wherein the ligand of the rhodium-phosphite complex catalyst is a phosphite compound of the following formula (5):

$$P(OR_1)(OR_2)(OR_3) \qquad (5)$$

wherein each of $R_1$, $R_2$ and $R_3$ which are independent of one another, is an organic group, provided that at least one of them is a substituted-2-naphthyl group of the following formula (7):

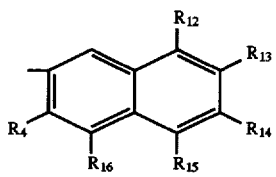

(7)

wherein $R_4$ is a group of the formula $C(R_9)(R_{10})(R_{11})$ or an aryl group which may have a substituent, wherein each of $R_9$, $R_{10}$ and $R_{11}$ which may be the same or different from one another, is a hydrogen atom, a hydrocarbon group or a fluorinated hydrocarbon group, and each of $R_{12}$, $R_{13}$, $R_{14}$, $R_{15}$ and $R_{16}$ which may be the same or different from one another, is a hydrogen atom or an organic group.

9. The method for producing aldehydes according to claim 7, wherein the ligand of the rhodium-phosphite complex catalyst is a phosphite compound of the following formula (8):

$$A_1[-O-P(OR_{17})OR_{18}]_n \qquad (8)$$

wherein each of $R_{17}$ and $R_{18}$ which may be the same or different from each other, is an aromatic hydrocarbon group, provided that at least one of the aromatic hydrocarbon groups has a hydrocarbon group on a carbon atom adjacent to the carbon atom bonded to an oxygen atom, $A_1$ is a n-valent organic group containing an aliphatic hydrocarbon, alicyclic hydrocarbon or aromatic hydrocarbon partial structure which may have a substituent, the respective [—O—P($OR_{17}$)($OR_{18}$)] groups may be the same or different from one another, and n is an integer of from 2 to 4.

10. The method for producing aldehydes according to claim 7, wherein an amine is present in the separating operation for at least one component.

11. The method for producing aldehydes according to claim 10, wherein the amine is a higher boiling point substance than the aldehyde product.

12. The method for producing aldehydes according to claim 10, wherein the amine is a tertiary amine.

13. The method for producing aldehydes according to claim 10, wherein the amine is present in an amount of from 1 to 20 mols per mol of rhodium.

14. The method for producing aldehydes according to claim 1, wherein the olefinic unsaturated compound is selected from the group consisting of propylene, butenes, octenes and nonenes.

15. The method for producing aldehydes according to claim 14, wherein the olefinic unsaturated compound is propylene.

16. A method for producing aldehydes, which comprises reacting an olefinic unsaturated compound with carbon monoxide and hydrogen for hydroformylation in the presence of a rhodium-phosphite complex catalyst to obtain a reaction product solution containing the rhodium-phosphite complex catalyst and an aldehyde product, and separating from the reaction product solution at least one component selected from the group consisting of carbon monoxide, hydrogen, an unreacted olefinic unsaturated compound, the aldehyde product, a solvent, a medium-boiling by-product and a high-boiling by-product by a separating operation, wherein at least one separating operation is carried out substantially in the presence of water, and the temperature, the residence time and the steam fraction in the separating operation are selected to be within such ranges that value P calculated from the following formula (3) would be at most 1:

$$P=1.0\times10^6\times\exp[-6000/(T_2+273)]\times\theta T_2\times X \qquad (3)$$

where $T_2$ is the maximum temperature (°C.) in the separating operation, $\theta T_2$ is the residence time (minutes) of the liquid in the separating operation, and X is the steam fraction defined by (the amount of steam)/(the amount of feed+the amount of steam).

17. The method for producing aldehydes according to claim 16, wherein the maximum temperature, the residence time and the steam fraction in the separating operation are selected to be within such ranges that value P calculated from the following formula (4) would be at most 1:

$$P=1.8\times10^6\times\exp[-6000/(T_2+273)]\times\theta T_2\times X \qquad (4)$$

where $T_2$ is the maximum temperature (°C.) in the separating operation, $\theta T_2$ is the residence time (minutes) of the liquid in the separating operation, and X is the steam fraction defined by (the amount of steam)/(the amount of feed+the amount of steam).

18. The method for producing aldehydes according to claim 16, wherein the separating operation is steam distillation, wherein $T_2$ is the bottom temperature (°C.) of the steam distillation, and the residence time $\theta T_2$ is the residence time (minutes) in the distillation still.

19. The method for producing aldehydes according to claim 16, wherein the separating operation is an operation for separating the aldehyde product.

20. The method for producing aldehydes according to claim 16, wherein the temperature $T_2$ in the separating operation is from 40° to 180° C., the residence time $\theta T_2$ is from 0.01 to 180 minutes, and the steam fraction X is from 0.1 to 0.9.

21. The method for producing aldehydes according to claim 16, wherein the ligand of the rhodium-phosphite complex catalyst is a cyclic or non-cyclic monophosphite compound.

22. The method for producing aldehydes according to claim 16, wherein at least one alcohol component of the phosphite compound is an aromatic alcohol having a hydrocarbon substituent on a carbon atom adjacent to the carbon atom bonded to an oxygen atom.

23. The method for producing aldehydes according to claim 16, wherein the ligand of the rhodium-phosphite complex catalyst is a phosphite compound having no cyclic structure containing a phosphorus atom in its molecule.

24. The method for producing aldehydes according to claim 23, wherein the ligand of the rhodium-phosphite complex catalyst is a phosphite compound of the following formula (5):

$$P(OR_1)(OR_2)(OR_3) \qquad (5)$$

wherein each of $R_1$, $R_2$ and $R_3$ which are independent of one another, is an organic group, provided that at least one of them is a substituted-2-naphthyl group of the following formula (7):

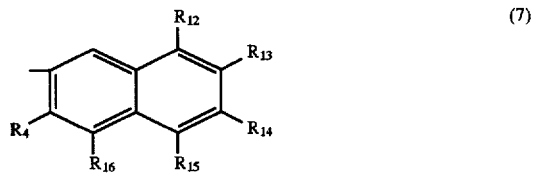

(7)

wherein $R_4$ is a group of the formula $C(R_9)(R_{10})(R_{11})$ or an aryl group which may have a substituent, wherein each of $R_9$, $R_{10}$ and $R_{11}$ which may be the same or different from one another, is a hydrogen atom, a hydrocarbon group or a fluorinated hydrocarbon group, and each of $R_{12}$, $R_{13}$, $R_{14}$, $R_{15}$ and $R_{16}$ which may be the same or different from one another, is a hydrogen atom or an organic group.

25. The method for producing aldehydes according to claim 23, wherein the ligand of the rhodium-phosphide complex catalyst is a phosphite compound of the following formula (8):

$$A_1[-O-P(OR_{17})OR_{18})]_n \qquad (8)$$

wherein each of $R_{17}$ and $R_{18}$ which may be the same or different from each other, is an aromatic hydrocarbon group, provided that at least one of the aromatic hydrocarbon groups has a hydrocarbon group on a carbon atom adjacent to the carbon atom bonded to an oxygen atom, $A_1$ is a n-valent organic group containing an aliphatic hydrocarbon, alicyclic hydrocarbon or aromatic hydrocarbon partial structure which may have a substituent, the respective [—O—P(OR_{17})(OR_{18})] groups may be the same or different from one another, and n is an integer of from 2 to 4.

26. The method for producing aldehydes according to claim 23, wherein an amine is present in the separating operation for at least one component.

27. The method for producing aldehydes according to claim 16, wherein the olefinic unsaturated compound is selected from the group consisting of propylene, butenes, octenes and nonenes.

28. The method for producing aldehydes according to claim 27, wherein the olefinic unsaturated compound is octenes.

* * * * *